United States Patent
Delporte et al.

(10) Patent No.: US 11,969,484 B2
(45) Date of Patent: Apr. 30, 2024

(54) COMPOSITION CONTAINING A SOMATOSTATIN ANALOGUE FOR RADIOPHARMACEUTICAL USE

(71) Applicant: Ariceum Therapeutics GmbH, Berlin (DE)

(72) Inventors: Marie Delporte, Dreux (FR); Sabine Hovest, Berlin (DE); Jens Kaufmann, Berlin (DE); Dennis Mewis, Berlin (DE); Anne Petit, Dreux (FR); Joel Richard, Dreux (FR)

(73) Assignee: Ariceum Therapeutics GmbH (DE)

( * ) Notice: Subject to any disclaimer, the term of this patent is extended or adjusted under 35 U.S.C. 154(b) by 122 days.

(21) Appl. No.: 17/251,426

(22) PCT Filed: Jun. 20, 2019

(86) PCT No.: PCT/EP2019/066329
§ 371 (c)(1),
(2) Date: Dec. 11, 2020

(87) PCT Pub. No.: WO2019/243489
PCT Pub. Date: Dec. 26, 2019

(65) Prior Publication Data
US 2023/0181771 A1    Jun. 15, 2023

(30) Foreign Application Priority Data

Jun. 21, 2018   (EP) .................................. 18179052

(51) Int. Cl.
*A61K 51/08* (2006.01)
*A61K 9/19* (2006.01)

(52) U.S. Cl.
CPC .............. *A61K 51/088* (2013.01); *A61K 9/19* (2013.01)

(58) Field of Classification Search
CPC ...... A61K 51/00; A61K 51/08; A61K 51/088; A61K 9/00; A61K 9/19
USPC .......... 424/1.11, 1.65, 1.69, 1.81, 1.85, 1.89, 424/9.1, 9.2, 9.3, 9.32, 9.4, 9.5; 530/300, 530/311, 328; 514/1, 11.1, 19.2, 21.7; 534/7, 10–14
See application file for complete search history.

(56) References Cited

U.S. PATENT DOCUMENTS 6,277,356 B1   8/2001   Albert et al.
2011/0269683 A1   11/2011   Rivier et al.

FOREIGN PATENT DOCUMENTS

| EP | 3015462 A1 * | 5/2016 | ........... C07D 255/02 |
| WO | 2008048942 A2 | 4/2008 | |
| WO | 2016077061 A2 | 5/2016 | |
| WO | WO-2018065634 A1 * | 4/2018 | ............. A61K 33/26 |

OTHER PUBLICATIONS

ChemBK, DOTA-JR-11 (2 pages), https://www.chembk.com/en/chem/1039726-31-2 (Year: 2015).*
Dalm et al, J Nucl. Med, vol. 58, pp. 1609-1614 (Year: 2017).*
Fani et al., Journal of Nuclear Medicine, 53:1481-1489 (2012).
Zamora et al., Applied Radiation and Isotopes, 48: 305-309 (1997).
Kang, et al., "Rapid Formulation Development of Monoclonal Antibodies," URL: https://bioprocessintl.com/manufacturing/formulation/rapid-formulation-development-for-monoclonal-antibodies/; 2016.
Wang, et al., "Antibody Structure, Instability, and Formulation," Journal of Pharmaceutical Sciences. 2007;96(1):1-26.
Chen, B., et al., "Influence of Histidine on the Stability and Physical Properties of a Fully Human Antibody in Aqueous and Solid Forms," Pharm Res. 2003;20(12):1952-60.
Molina, M.D., et al., "Formulation Strategies to Minimize Oxidative Damage in Lyophilized Lipid/DNA Complexes During Storage," J Pharm Sci. 2008; 97(12):5089-105.
Asti, M., et al., "Development of a Simple Kit-Based Method for Preparation of Pharmaceutical-Grade 68Ga-DOTATOC," Nucl Med Commun. 2015;36(5):502-10.

* cited by examiner

*Primary Examiner* — D. L. Jones
(74) *Attorney, Agent, or Firm* — Dechert LLP; Andrew T. Wilkins (57) ABSTRACT

The present invention relates to a somatostatin analogue composition for radiopharmaceutical use, in particular for diagnostic or therapeutic use. More specifically the somatostatin analogue is a receptor-selective somatostatin peptide antagonist.

19 Claims, 1 Drawing Sheet

COMPOSITION CONTAINING A SOMATOSTATIN ANALOGUE FOR RADIOPHARMACEUTICAL USE

The present application is a U.S. national stage filing of PCT/EP2019/066329, filed Jun. 20, 2019, which claims the priority benefit of European Application No. 18179052.8, filed Jun. 21, 2018. The contents of each of these applications is incorporated herein by reference.

The present invention relates to a somatostatin analogue composition for radiopharmaceutical use, in particular for diagnostic or therapeutic use. More specifically the somatostatin analogue is a receptor-selective somatostatin peptide antagonist.

The cyclic tetradecapeptide somatostatin-14 (SRIF) affects multiple cellular processes and is also known to inhibit the growth of certain tumors. SRIF induces its biological effects by interacting with a family of membrane-bound structurally similar receptors. Among the five SRIF receptors that have been cloned and are referred to as SSTR1-5, SSTR2 is believed to mediate the inhibition of growth hormone, glucagon and gastric acid secretion. Somatostatin receptors are expressed in pathological states, particularly in neuroendocrine tumors of the gastrointestinal tract and can be identified using in vitro binding methods or using in vivo imaging techniques, the latter allowing the precise localization of the tumors and their metastasis in the patients. Because somatostatin receptors in gastroenteropancreatic tumors are functional, their identification can be used to assess the therapeutic efficacy of an analogue to inhibit excessive hormone release in the patients.

A class of somatostatin peptide analogues which are highly SSTR2 selective and antagonists of somatostatin, although not internalized in cells having SSTR2 receptors, are described in WO 2008/048942. Such peptides bind selectively to cloned SSTR2 without activating the receptor, and these peptide analogues, when iodinated or otherwise radiolabeled, will retain their desirable biological properties. Thus, these peptides are useful in determining the tissue location and cellular expression of the receptor SSTR2.

Thus these peptides can be readily radiolabeled and effectively used in drug screening, imaging, diagnosis and/or radionuclide therapy. For example, these peptides carrying detectable labels are useful in localizing such receptors in the body and in diagnosing the locations of tumors, particularly neuroendocrine tumors.

However, there is a need for appropriate formulations for such peptides. Notably there is a need for a formulation having a long shelf-life for handling storage and dispatch, which also enables an efficient radiolabeling of such peptides with radionuclides before administration. There is also a need for a formulation which allows the peptides to remain stable after radiolabeling despite the radiolysis due to the radiation emission from the radionuclides.

The applicant has found a formulation containing such peptides coupled with a chelator, which allows the peptides to remain stable before and after radiolabeling (i.e. after complexation with a radionuclide). After radiolabeling, the role of the formulation is to minimize the degradation caused by radioactive emission of the radionuclides.

By "stable", it is meant in the context of the present invention that the content in peptides is maintained over time. Before radiolabeling, the formulation allows the peptides to remain stable for at least 3 months, preferably at least 12 months, at appropriate storage conditions. After radiolabeling, the formulation allows the peptides to remain stable for at least 1 day at appropriate storage conditions.

The present invention relates to a composition for radiopharmaceutical use, such composition containing at least one receptor-selective somatostatin peptide antagonist, in particular the peptide with an amino acid sequence presented below (INN: satoreotide):

H-Phe-(D-Cys)-Phe-(D-Phe)-Lys-Thr-Cys-(D-Tyr)-NH$_2$

This peptide may directly be coupled at its N-terminus with a chelator, and in particular with the chelator NODAGA (1-(1,3-carboxypropyl)-1,4,7-triazacyclononane-4,7-diacetic acid).

The peptide coupled at its N-terminus with chelator NODAGA (hereafter called "NODAGA-peptide", INN: satoreotide trizoxetan) has the following structure:

—Phe-(D-Cys)-Phe-(D-Phe)-Lys-Thr-Cys-(D-tyr)-NH$_2$

NODAGA-peptide may be in the form of a salt or a free base. Generally, when a percentage or concentration of NODAGA-peptide is given, the value is indicated in equivalent free base, even if it is in the form of a salt in the formulation.

NODAGA-peptide may be used as a precursor of a radiolabeled compound and thus may be further complexed with or conjugated to an appropriate radionuclide, such as $^{68}$Ga$^{3+}$ cation.

The present invention provides a receptor-selective somatostatin peptide antagonist composition, said composition comprising:

NODAGA-peptide, or a salt thereof,
an antioxidant, and
a bulking agent.

More preferably, the composition of the present invention comprises:
NODAGA-peptide, or a salt thereof,
an antioxidant,
a bulking agent, and
a surfactant.

Unless otherwise indicated, the following definitions are set forth to illustrate and define the meaning and scope of the various terms used to describe the invention herein.

Unless otherwise stated, all percentages mentioned in the present invention are weight percentages (w/w).

The term "active ingredient" refers to NODAGA-peptide compound described above, eventually complexed with a radionuclide (i.e. radiolabeled).

The term "antioxidant" means a compound having antioxidant properties in order to prevent oxidative degradation reaction, such as redox processes, of the active ingredient and/or the excipients, notably under radiation emission. In particular, it is a free radical scavenger, which traps highly-reactive free radicals, such as oxygen-containing free radicals arising from the radiolysis of water.

The term "bulking agent" as used herein refers to a compound or excipient, which facilitates material handling during a lyophilisation process and enables the formation of a solid cake with a regular surface.

The term "surfactant" as used herein refers to a compound or excipient with surface active properties, used mainly in the present compositions to improve the aqueous solubility of the active ingredient, limit adsorption at solid surfaces and interfaces, help to protect the active ingredient against degradation and/or limit in vitro active ingredient precipitation.

The term "buffering agent" as used herein refers to a weak acid or base used to maintain the pH of a solution near a chosen value after the addition of another acid or base or upon dilution. The function of a buffering agent is to prevent a rapid change in pH when acids or bases are added to a solution. The buffering agent also maintains the pH of the composition in the appropriate range to ensure stability and avoid degradation of the DOTA-peptide during processing and storage.

The term "buffer solution" as used herein refers to an aqueous solution containing a mixture of a weak acid and its conjugated base, or vice versa. The pH of a buffer solution changes very little when a small amount of strong acid or base is added to it. When lyophilized, a buffer solution yields the buffering agent or the system of buffering agents.

The term "tonicity agent" as used herein refers to an isotonic modifier or osmotic adjuster (or osmolyte) that provides osmolality to the buffer solution. Osmolality refers to the total osmotic activity contributed by ions and non-ionized molecules to a solution.

The term "solubilizing agent" as used herein means a pharmaceutical excipient used for providing or increasing solubility of the active ingredient in solvent, in particular in water.

The antioxidant may be an antioxidant or a mixture thereof. The antioxidant may be selected from ascorbic acid or a salt thereof, gentisic acid or a salt thereof, methionine, retinol, or ethanol. In a preferred embodiment, the antioxidant is selected from ascorbic acid or a salt thereof, and methionine. More preferably the antioxidant is ascorbic acid or a salt thereof.

The bulking agent may be a bulking agent or a mixture thereof. The bulking agent may be selected from sugar polyols such as mannitol; disaccharides such as sucrose, trehalose or maltose; polysaccharides such as dextrane; cyclodextrines; amino acids such as glycine; and mixtures thereof. In a preferred embodiment, the bulking agent is a disaccharide, and more preferably trehalose.

The tonicity agent may be a tonicity agent or a mixture thereof. The tonicity agent may be selected from inorganic salts such as sodium chloride and potassium chloride, mannitol, dextrose, polyethylene glycols (PEGs), polypropylene glycol, glycine, glycerol; and mixtures thereof.

The solubilizing agent may be a solubilizing agent or a mixture thereof. The solubilizing agent may be selected from polyethylene glycols, in particular polyethylene glycol 300 or polyethylene glycol 400, ethanol, propylene glycol, glycerine, polysorbates, in particular polysorbate 20 or polysorbate 80; and mixtures thereof.

The surfactant may be a surfactant or a mixture thereof. Preferably, the surfactant is a non-ionic surfactant. The surfactant may be selected from polysorbates such as polysorbate 20, polysorbate 40, polysorbate 60, polysorbate 80, or a mixture thereof; poloxamers such as poloxamer 188 or mixture thereof. In a preferred embodiment, the surfactant is a polysorbate, also called ethoxylated sorbitan ester of fatty acid. More, preferably, the surfactant is polysorbate 80 (polyoxyethylene (20) sorbitan monooleate).

The salts of NODAGA-peptide which can be used for the invention are preferably pharmaceutically acceptable salts of organic acids, such as those of acetic, fumaric, gluconic, alginic, maleic, citric, malic, pamoic, ascorbic, succinic, tartric, or benzoic acids, or pharmaceutically acceptable salts of inorganic acids, such as those of hydrochloric, hydrobromic, hydriodic, sulphuric or phosphoric acids. In a preferred embodiment, NODAGA-peptide is in a salt form, and is preferably NODAGA-peptide acetate salt.

The term "radiopharmaceutical" is a term well known to a person skilled in the art of nuclear medicine and refers to any chemical or biological agent that comprises a radionuclide having emissions suitable for detection or treatment of malignant diseases. Radiopharmaceuticals may be used for in vivo imaging or for radiotherapy, preferably receptor-targeted radiotherapy.

The compositions of the invention are preferably pharmaceutical compositions, meaning that the excipients and salts described herein are biocompatible excipients and biocompatible salts.

Preferably, in the composition of the present invention:
the antioxidant is selected from ascorbic acid or a salt thereof and methionine,
the bulking agent is a disaccharide, and
the surfactant is a polysorbate.

More preferably, the composition of the present invention comprises:
NODAGA-peptide, or a salt thereof,
an antioxidant selected from ascorbic acid or a salt thereof,
a bulking agent selected from a disaccharide, and
a surfactant selected from a polysorbate.

Preferably, in the composition of the present invention, the weight ratio of the antioxidant over NODAGA-peptide is of at least 50, more preferably comprised from 50 to 150, advantageously comprised from 75 to 125.

Preferably, in the composition of the present invention, the weight ratio of the bulking agent over NODAGA-peptide is of at least 500, more preferably comprised from 500 to 1500, advantageously comprised from 750 to 1250.

Lyophilized Composition

According to a first embodiment, the composition according to the invention is in a lyophilized form, also called "lyophilized composition (I)".

A lyophilized composition (I) according to this embodiment comprises less than 5%, preferably less than 4%, preferably less than 3%, preferably less than 2%, preferably less than 1% by weight of water relative to the total weight of the lyophilized composition.

In order to obtain a radiolabeled formulation ready for radiopharmaceutical use, a lyophilized composition (I) according to this embodiment may be reconstituted with an appropriate reconstitution solution (such as water or a buffer solution) before the addition of a radionuclide in solution.

Preferably, according to this first embodiment, the lyophilized composition (I) of the present invention comprises:
NODAGA-peptide, in a salt form,
ascorbic acid or a salt thereof,
a disaccharide, and
a polysorbate.

Preferably, in the lyophilized composition (I), the NODAGA-peptide is in a salt form and is present in the range of 0.02% to 0.20% by weight relative to the total weight of the composition, preferably from 0.03% to 0.15%, more preferably from 0.04% to 0.12%.

Preferably, NODAGA-peptide in a salt form is present in the range of 0.08% to 0.10% by weight relative to the total weight of the composition.

Preferably, NODAGA-peptide is an acetate salt and is present in the lyophilized composition (I) in the range of 0.08% to 0.10% by weight relative to the total weight of the composition.

Preferably, the lyophilized composition (I) comprises an antioxidant present in the range of 4% to 15% by weight relative to the total weight of the composition, preferably from 6% to 12%, more preferably from 8% to 10%.

Preferably, the lyophilized composition (I) comprises ascorbic acid present in the range of 4% to 15% by weight relative to the total weight of the composition, preferably from 6% to 12%, more preferably from 8% to 10%.

Preferably, the lyophilized composition (I) comprises a bulking agent present in the range of 80% to 96% by weight relative to the total weight of the composition, preferably from 85% to 95%, more preferably from 88% to 94%.

Preferably, the lyophilized composition (I) comprises a disaccharide present in the range of 80% to 96% by weight relative to the total weight of the composition, preferably from 85% to 95%, more preferably from 88% to 94%.

More preferably, the disaccharide is present in the range of 89% to 93% by weight relative to the total weight of the composition, and more preferably the disaccharide is trehalose.

Preferably, the lyophilized composition (I) comprises a surfactant present in the range of 0.01% to 0.36% by weight relative to the total weight of the composition, preferably in the range of 0.10% to 0.25%, more preferably lower than 0.20%.

Preferably, the lyophilized composition (I) comprises a polysorbate present in the range of 0.01% to 0.36% by weight relative to the total weight of the composition, preferably in the range of 0.10% to 0.25%, more preferably lower than 0.20%.

More preferably, the polysorbate is present in the range of 0.16% to 0.20% by weight relative to the total weight of the composition, and more preferably the polysorbate is polysorbate 80.

Preferably, NODAGA-peptide, antioxidant, bulking agent and surfactant, taken together, represent at least 95% by weight of the total weight of the lyophilized composition (I), preferably at least 98%, and more preferably at least 99%.

Preferably, according to this first embodiment, the lyophilized composition (I) of the present invention comprises:
NODAGA-peptide in a salt form,
ascorbic acid,
a disaccharide, and
a polysorbate,
wherein NODAGA-peptide in the salt form, ascorbic acid, the disaccharide and the polysorbate, taken together, represent at least 98% of the total weight of the lyophilized composition.

Preferably, according to this first embodiment, the lyophilized composition (I) of the present invention comprises:
NODAGA-peptide acetate salt in the range of 0.02% to 0.20% by weight,
ascorbic acid in the range of 4% and 15% by weight,
a disaccharide in the range of 80% to 96% by weight, and
a polysorbate in the range of 0.10% to 0.36% by weight,
wherein NODAGA-peptide acetate salt, ascorbic acid, the disaccharide and the polysorbate, taken together, represent at least 98% of the total weight of the lyophilized composition.

More preferably, the lyophilized composition (I) of the present invention comprises:
NODAGA-peptide acetate salt in the range of 0.03% to 0.15% by weight,
ascorbic acid in the range of 6% and 12% by weight,
a disaccharide in the range of 85% to 95% by weight, and
a polysorbate in the range of 0.10% to 0.25% by weight,
wherein NODAGA-peptide acetate salt, ascorbic acid, the disaccharide and the polysorbate, taken together, represent at least 98% of the total weight of the lyophilized composition.

More preferably, according to this first embodiment, the dry ingredients of the lyophilized composition (I) of the present invention consist in:
NODAGA-peptide acetate salt in the range of 0.08% to 0.10% by weight,
ascorbic acid in the range of 8% and 10% by weight,
trehalose in the range of 89% to 93% by weight,
polysorbate 80 in a range of 0.16% to 0.20% by weight.

The lyophilized composition (I) of the invention has the advantage of having a very good stability, meaning that the content of NODAGA-peptide is maintained over time. Such a lyophilized composition having an extended shelf-life, it is particularly advantageous for the development, manufacturing, storage and distribution to the patients of the corresponding radiopharmaceutical drug.

According to a variant of this first embodiment, the lyophilized composition (I) also comprises one or more additives selected from buffering agents, tonicity agents, and solubilizing agents, which are also in dry or lyophilized form.

In order to obtain a radiolabeled formulation ready for radiopharmaceutical use, a lyophilized composition (I) according to this variant may be reconstituted with an appropriate radiolabeling solution, which may be an acidic solution of $^{68}Ga^{3+}$ cations, such as the one obtained by eluting a 0.05-0.1M HCl solution from a $^{68}Ge/^{68}Ga$ generator or by using a $^{68}Ga$-producing cyclotron.

According to a preferred variant, the lyophilized composition (I) also comprises a buffering agent. A lyophilized composition according to this variant is called lyophilized composition (I').

A lyophilized composition (I') according to this preferred variant may be obtained by mixing a lyophilized composition (I) and a buffer solution, followed by lyophilisation of the mixture.

According to this preferred variant, NODAGA-peptide, the antioxidant, the bulking agent, the surfactant and the buffering agent, taken together, represent at least 98% by weight of the total weight of the lyophilized composition (I'), and more preferably at least 99% by weight.

According to this preferred variant, the dry ingredients of the lyophilized composition (I') preferably consist in:
NODAGA-peptide acetate salt,
ascorbic acid,
a disaccharide,
a polysorbate,
buffering agent.

The buffering agent of the lyophilized composition (I') according to this variant is preferably an acetic acid/sodium acetate buffering agent, more preferably such that, after reconstitution of the lyophilized composition (I') with water the pH of the mixture is comprised from 4 and 6, and preferably between 4.5 and 5.5, and more preferably between 4.8 and 5.2. This pH is particularly suitable for the radiolabeling of NODAGA-peptide with $^{68}$Ga.

Liquid Composition

According to a second embodiment, the composition according to the invention is in a liquid form, and is called "liquid composition (II)".

The liquid phase of the liquid composition (II) is mainly composed of water. The liquid composition (II) can also be characterized as an aqueous solution wherein the active ingredient and the excipients are solubilized.

A liquid composition (II) according to the present invention may typically be obtained by reconstitution of a lyophilized composition (I) according to the invention with a reconstitution solution, which may be a buffer solution.

A liquid composition (II) according to the present invention may also be obtained by rehydration of a lyophilized composition (I') according to the invention.

Preferably, according to this second embodiment, the liquid composition (II) of the invention comprises:
NODAGA-peptide, or a salt thereof,
at least one excipient selected from an antioxidant, a bulking agent and a surfactant, and
a buffer solution.

Preferably, according to this second embodiment, the liquid composition (II) of the invention comprises:
NODAGA-peptide, or a salt thereof, and
at least two excipients selected from antioxidant, bulking agent, surfactant and mixture thereof, and
a buffer solution.

Preferably, according to this second embodiment, the liquid composition (II) of the invention comprises:
NODAGA-peptide in a salt form,
an antioxidant,
a bulking agent,
a surfactant, and
a buffer solution.

Preferably, according to this second embodiment, the liquid composition (II) of the invention comprises:
NODAGA-peptide in a salt form,
ascorbic acid,
a disaccharide,
a polysorbate, and
a buffer solution.

The following mg/mL concentrations are given in weight relative to the total volume of the liquid composition (II).

Preferably, the liquid composition (II) according to the present invention comprises the NODAGA-peptide in a salt form at a concentration of 0.02 to 0.12 mg/mL, preferably at a concentration of 0.03 to 0.10 mg/mL, more preferably at a concentration of 0.04 to 0.06 mg/mL.

More preferably, NODAGA-peptide in a salt form is at the concentration of 0.045 to 0.055 mg/mL.

Advantageously, NODAGA-peptide is an acetate salt at the concentration of 0.02 to 0.12 mg/mL, 0.03 to 0.10 mg/mL, 0.04 to 0.06 mg/mL or 0.045 to 0.055 mg/mL.

Preferably, the liquid composition (II) according to the present invention comprises an antioxidant at a concentration of 2 to 10 mg/mL, preferably at a concentration of 3 to 8 mg/mL, more preferably at a concentration of 4 to 6 mg/mL.

Preferably, the liquid composition (II) according to the present invention comprises ascorbic acid at a concentration of 2 to 10 mg/mL, preferably at a concentration of 3 to 8 mg/mL, more preferably at a concentration of 4 to 6 mg/mL.

In a preferred embodiment, ascorbic acid is at the concentration of 4.5 to 5.5 mg/mL.

Preferably, the liquid composition (II) according to the present invention comprises a bulking agent at a concentration of 20 to 120 mg/mL, preferably at a concentration of 30 to 80 mg/mL, more preferably at a concentration of 40 to 60 mg/mL.

Preferably, the liquid composition (II) according to the present invention comprises a disaccharide at a concentration of 20 to 120 mg/mL, preferably at a concentration of 30 to 80 mg/mL, more preferably at a concentration of 40 to 60 mg/mL. In a preferred embodiment, the disaccharide is at the concentration of 45 to 55 mg/mL, and more preferably the disaccharide is trehalose at the concentration of 45 to 55 mg/mL.

Preferably, the liquid composition (II) according to the present invention comprises a surfactant at a concentration of 0.05 to 0.2 mg/mL, preferably at a concentration of 0.05 to 0.15 mg/mL, more preferably at a concentration of 0.075 to 0.125 mg/mL.

Preferably, the liquid composition (II) according to the present invention comprises a polysorbate at a concentration of 0.05 to 0.2 mg/mL, preferably at a concentration of 0.05 to 0.15 mg/mL, more preferably at a concentration of 0.075 to 0.125 mg/mL. In a preferred embodiment, the polysorbate is at the concentration of 0.08 to 0.12 mg/mL, and more preferably the polysorbate is polysorbate 80 at the concentration of 0.08 to 0.12 mg/mL.

Preferably, the liquid composition (II) according to the present invention comprises a buffer solution that is selected to reach a pH between 4 and 6, and preferably between 4.5 and 5.5, and more preferably between 4.8 and 5.2. The buffer solution is preferably an acetate buffer solution, more preferably an acetate buffer solution at 1 M concentration.

The liquid composition (II) may optionally further comprise additives such as alternative antioxidants and/or alternative buffering agents. In a preferred embodiment, NODAGA-peptide, the antioxidant, the bulking agent, the surfactant and the buffer solution, taken together, represent at least 95, 98 or 99% by weight relative to the total weight of the liquid composition (II).

Preferably, according to this second embodiment, the liquid composition (II) of the invention comprises:
NODAGA-peptide in a salt form,
ascorbic acid,
a disaccharide,
a polysorbate, and
a buffer solution, wherein NODAGA-peptide in the salt form, ascorbic acid, the disaccharide, the polysorbate and the buffer solution, taken together, represent at least 98% by weight of the total weight of the composition.

Preferably, according to this second embodiment, the liquid composition (II) of the invention comprises:
NODAGA-peptide acetate salt at a concentration of 0.02 to 0.12 mg/mL,
ascorbic acid at a concentration of 2 to 10 mg/mL,
a disaccharide at a concentration of 20 to 120 mg/mL,
a polysorbate at a concentration of 0.05 to 0.2 mg/mL, and
a buffer solution,
wherein NODAGA-peptide acetate salt, ascorbic acid, the disaccharide, the polysorbate and the buffer solution, taken together, represent at least 98% by weight of the total weight of the composition.

Preferably, the liquid composition (II) of the present invention comprises:
NODAGA-peptide acetate salt at a concentration of 0.03 to 0.1 mg/mL,
ascorbic acid at a concentration of 3 to 8 mg/mL,
a disaccharide at a concentration of 30 to 80 mg/mL,
a polysorbate at a concentration of 0.05 to 0.15 mg/mL, and
a buffer solution,
wherein NODAGA-peptide acetate salt, ascorbic acid, the disaccharide, the polysorbate and the buffer solution, taken together, represent at least 98% by weight of the total weight of the composition.

More preferably, the liquid composition (II) of the present invention comprises:
NODAGA-peptide acetate salt at a concentration of 0.04 to 0.06 mg/mL,
ascorbic acid at a concentration of 4 to 6 mg/mL,
a disaccharide at a concentration of 40 to 60 mg/mL,
a polysorbate at a concentration of 0.075 to 0.125 mg/mL, and
a buffer solution,
wherein NODAGA-peptide acetate salt, ascorbic acid, the disaccharide, the polysorbate and the buffer solution, taken together, represent at least 98% by weight of the total weight of the composition.

More preferably, according to this second embodiment, the liquid composition (II) of the invention consists in:
NODAGA-peptide acetate salt at a concentration of 0.045 to 0.055 mg/mL,
ascorbic acid at a concentration of 4.5 to 5.5 mg/mL,
trehalose at a concentration of 45 to 55 mg/mL,
polysorbate 80 at a concentration of 0.08 to 0.12 mg/mL, and
acetate buffer solution.

Radiolabeled Composition

According to a third embodiment, the composition according to the invention is a radiolabeled composition (III), ready for radiopharmaceutical use.

The radiolabeled composition (III) of the invention is preferably a radiopharmaceutical composition, suitable for injection in mammals.

In a radiolabeled composition (III) according to the invention, the NODAGA-peptide is at least partly radiolabeled, i.e. complexed with a radionuclide cation.

A radiolabeled composition (III) according to the invention may be obtained by radiolabeling a liquid composition (II) according to the invention.

Alternatively, a radiolabeled composition (III) according to the invention may be directly obtained by radiolabeling of a lyophilized composition (I') according to the invention wherein said lyophilized composition (I') already comprises a buffering agent.

The radiolabeling process is well known by the skilled person in the art and is typically carried out by mixing the liquid composition (II) or the lyophilized composition (I') with a radionuclide cationic salt in solution. Usually, the NODAGA-peptide is in molar excess relative to the radionuclide cation, in order to maximize the complexation of the radionuclide cation by the NODAGA chelator.

Suitable radionuclides include radionuclides useful in imaging techniques and/or in therapeutic indications.

Suitable radionuclides useful in imaging include, without limitation, the γ-emitting radionuclides for Single Photon Emission Tomography (SPECT) and the positron-emitting radionuclides for Positron Emission Tomography (PET). The γ-emitting radionuclides include, without limitation, $^{67}$Ga, $^{111}$In, $^{177}$Lu, $^{99m}$Tc, and $^{123}$I. The positron-emitting radionuclides include, without limitation, $^{64}$Cu, $^{18}$F, $^{44}$Sc, and $^{68}$Ga.

Suitable nuclides useful in therapeutic indications include, without limitation, the β-emitting radionuclides. Such β-emitting radionuclides may be selected from $^{90}$Y, $^{177}$Lu, and $^{188}$Re.

A preferred radionuclide for the NODAGA-peptide active ingredient is an imaging radionuclide, and more preferably an imaging positron-emitting radionuclide. A more preferred imaging radionuclide cation is $^{68}$Ga$^{3+}$.

Preferably, according to this third embodiment, the radiolabeled composition (III) of the invention comprises:
radiolabeled NODAGA-peptide,
an antioxidant,
a bulking agent,
a surfactant,
a buffer solution, and
optionally one or more pharmaceutically acceptable carriers or diluents.

Preferably, according to this third embodiment, the radiolabeled composition (III) of the invention comprises:
NODAGA-peptide complexed with a positron-emitting radionuclide, preferably useful in imaging techniques,
an antioxidant,
a bulking agent,
a surfactant,
a buffer solution, and
optionally one or more pharmaceutically acceptable carriers or diluents.

Preferably, in the radiolabeled composition (III), the NODAGA-peptide is complexed with $^{68}$Ga$^{3+}$.

Preferably, according to this third embodiment, the radiolabeled composition (III) of the invention comprises:
$^{68}$Ga$^{3+}$ radiolabeled NODAGA-peptide,
ascorbic acid,
a disaccharide,
a polysorbate, and
a buffer solution.

More preferably, according to this third embodiment, the radiolabeled composition (III) of the invention comprises and even more consists in:
$^{68}$Ga$^{3+}$ radiolabeled NODAGA-peptide,
ascorbic acid,
trehalose,
polysorbate 80, and
an acetate buffer solution.

In the radiolabeled composition (III) according to the present invention, the radiolabeling of NODAGA-peptide may not be quantitative. Therefore, the radiolabeled form of NODAGA-peptide and the non-radiolabeled form of NODAGA-peptide may co-exist in the radiolabeled composition (III) according to the present invention.

Preferably, in a radiolabeled composition (III) according to the present invention, the ratio $^{68}Ga^{3+}$ radiolabeled NODAGA-peptide vs non-radiolabeled NODAGA-peptide is lower than 40:60, 30:70, 20:80, 10:90, 5:95, 4:96, 3:97 or 2:98, and more preferably lower than 5:95, 4:96, 3:97, 2:98 or 1:99.

Preferably, in a radiolabeled composition (III) according to the present invention, the $^{68}Ga^{3+}$ radiolabeled and non-radiolabeled NODAGA-peptide (taken together) is at a concentration of 0.003 to 0.060 mg/mL, preferably at a concentration of 0.005 to 0.05 mg/mL, more preferably at a concentration of 0.0065 to 0.03 mg/mL.

Preferably, the $^{68}Ga^{3+}$ radiolabeled and non-radiolabeled NODAGA-peptide NODAGA-peptide (taken together) is at the concentration of 0.0075 to 0.0275 mg/mL.

Preferably, in a radiolabeled composition (III) according to the present invention, antioxidant is at a concentration of 0.30 to 5 mg/mL, preferably at a concentration of 0.5 to 4 mg/mL, more preferably at a concentration of 0.65 to 3.0 mg/mL.

Preferably, in a radiolabeled composition (III) according to the present invention, ascorbic acid is at a concentration of 0.30 to 5 mg/mL, preferably at a concentration of 0.5 to 4 mg/mL, more preferably at a concentration of 0.65 to 3.0 mg/mL. In a preferred embodiment, ascorbic acid is at the concentration of 0.75 to 2.75 mg/mL.

Preferably, in a radiolabeled composition (III) according to the present invention, bulking agent is at a concentration of 3 to 60 mg/mL, preferably at a concentration of 5 to 40 mg/mL, more preferably at a concentration of 6.5 to 30 mg/mL.

Preferably, in a radiolabeled composition (III) according to the present invention, the disaccharide is at a concentration of 3 to 60 mg/mL, preferably at a concentration of 5 to 40 mg/mL, more preferably at a concentration of 6.5 to 30 mg/mL. In a preferred embodiment, the disaccharide is at the concentration of 7.5 to 27.5 mg/mL, and more preferably the disaccharide is trehalose at the concentration of 7.5 to 27.5 mg/mL.

Preferably, in a radiolabeled composition (III) according to the present invention, surfactant is at a concentration of 0.008 to 0.1 mg/mL, preferably at a concentration of 0.008 to 0.075 mg/mL, more preferably at a concentration of 0.0125 to 0.065 mg/mL.

Preferably, in a radiolabeled composition (III) according to the present invention, the polysorbate is at a concentration of 0.008 to 0.1 mg/mL, preferably at a concentration of 0.008 to 0.075 mg/mL, more preferably at a concentration of 0.0125 to 0.065 mg/mL. In a preferred embodiment, the polysorbate is at the concentration of 0.013 to 0.06 mg/mL, and more preferably the polysorbate is polysorbate 80 at the concentration of 0.013 to 0.06 mg/mL.

Preferably, in a radiolabeled composition (III) according to the present invention, the buffer solution is an acetate buffer solution.

The radiolabeled composition (III) according to the present invention preferably comprises, and even more preferably consists in:
$^{68}Ga^{3+}$ radiolabeled NODAGA-peptide,
non-radiolabeled NODAGA-peptide,
an antioxidant,
a bulking agent,
a surfactant,
a buffer solution, and
optionally one or more pharmaceutically acceptable carriers or diluents.

The radiolabeled composition (III) preferably comprises, and even more preferably consists in:
$^{68}Ga^{3+}$ radiolabeled NODAGA-peptide,
non-radiolabeled NODAGA-peptide,
ascorbic acid,
a disaccharide,
a polysorbate, and
a buffer solution.

A radiopharmaceutical composition (III) more preferably comprises, and even more preferably consists in:
$^{68}Ga^{3+}$ radiolabeled NODAGA-peptide,
non-radiolabeled NODAGA-peptide,
ascorbic acid,
trehalose,
polysorbate 80, and
an acetate buffer solution,
wherein the ratio $^{68}Ga^{3+}$ radiolabeled NODAGA-peptide vs non-radiolabeled NODAGA-peptide is lower than 5:95.

In a preferred variant, the radiolabeled composition (III) of the present invention comprises and more preferably consists in:
$^{68}Ga^{3+}$ radiolabeled NODAGA-peptide and non-radiolabeled NODAGA-peptide acetate salt, taken together, at a concentration of 0.003 to 0.060 mg/mL,
ascorbic acid at a concentration of 0.30 to 5 mg/mL,
a disaccharide at a concentration of 3 to 60 mg/mL,
a polysorbate at a concentration of 0.008 to 0.1 mg/mL, and
an acetate buffer solution.

Process of Preparation

The manufacture of the lyophilized composition (I) preferably starts with the manufacture of NODAGA-peptide solution which typically consists first in dissolving all the excipients in water for injections. NODAGA-peptide is then dissolved in the excipients solution previously prepared, under stirring, until complete dissolution. The bulk NODAGA-peptide solution is usually sterilized by sterilizing filtration (for example through a 0.22 μm membrane filter) and then aseptically filled into sterile vials.

Lyophilization may then be carried out according to following procedure. Filled vials are loaded in a freeze dryer and lyophilized following a defined lyophilization cycle, vials are then stoppered under nitrogen in the freeze dryer and finally crimped with an aluminum seal.

The manufacture of the liquid composition (II) uses simple and conventional process unit operations. A buffer solution is first prepared, for example by mixing acetic acid and sodium acetate with water in a vial container. The buffer solution may be sterilized in the vial container by steam sterilization. It is then added to the lyophilized composition (I) for reconstitution.

The process for the preparation of the radiolabeled composition (III) comprises the complexation (also called radiolabeling) of the NODAGA-peptide with a radionuclide in solution. Such complexation may be performed at room temperature or elevated temperatures by mixing a solution of a radionuclide cation, preferably the eluate from a $^{68}Ge/^{68}Ga$-generator or cyclotron produced $^{68}Ga^{3+}$, with the liquid composition (II), at pH 3 to 6. The complexation of the radionuclide cation, preferably $^{68}Ga^{3+}$, occurs instantaneously by the chelator moiety of the NODAGA-peptide.

During the radiolabeling process, the NODAGA-peptide is generally in excess relative to the radionuclide. In particular, during the process of complexation with the radionuclide cation $^{68}Ga^{3+}$, the NODAGA-peptide is in excess which gives a ratio $^{68}Ga^{3+}$ radiolabeled NODAGA-peptide vs non-radiolabeled NODAGA-peptide preferably lower than 10:90, 5:95, 4:96, 3:97, 2:98, 1:99, or even lower.

Kit

Another aspect of the present invention is a kit for the preparation of a radiopharmaceutical composition, said kit comprising at least a suitable container containing a lyophilized composition (I) as defined above.

In a preferred embodiment, the kit of the invention comprises:
a first vial containing a lyophilized composition (I) or (I') as defined above, and
a second vial containing a sterile reconstitution solution.

The reconstitution solution may comprise water for injections, buffering agent, alcohol such as ethanol, and antioxidant. The antioxidant may be selected from ascorbic acid or a salt thereof, gentisic acid or a salt thereof, methionine, retinol, cysteine, N-acetyl cysteine, propyl gallate and mixtures thereof. The buffering agents may be selected from acetic acid and its salts, citric acid or its salts, ascorbic acid and its salts, and mixtures thereof. The buffering agent is selected to reach an appropriate pH to ensure that the pH of the radiopharmaceutical composition is within acceptable range for human administration and also to ensure the appropriate conditions for the radiolabeling process.

In a preferred embodiment, the reconstitution solution is a buffer solution, and more preferably an acetate buffer solution, with a pH advantageously comprised from 4 and 6, and preferably between 4.5 and 5.5, and more preferably between 4.8 and 5.2.

In a preferred embodiment, the kit of the invention comprises:
a first vial containing a lyophilized composition (I) as defined above, and
a second vial containing a sterile reconstitution solution comprising a buffer solution, preferably an acetate buffer solution.

Preferably, the kit comprises:
a first vial containing a lyophilized composition (I) comprising:
NODAGA-peptide acetate salt in the range of 0.08% to 0.10% by weight,
ascorbic acid in the range of 8 and 10% by weight,
trehalose in the range of 89 to 93% by weight,
polysorbate 80 in a range of 0.16 to 0.20% by weight, and
optionally nitrogen (qs), and
a second vial containing a sterile reconstitution solution of an acetate buffer solution.

In another embodiment, the kit of the invention comprises:
a first vial containing a lyophilized composition (I') as defined above, and
a second vial containing a sterile reconstitution solution comprising water.

The kit may also contain instructions for mixing the content of the two vials and then complexing with a radionuclide in solution.

The kit of the present invention with the lyophilized composition (I) is advantageously a ready-to-use kit as it can be used with a radionuclide without any addition of further excipients or additives during the preparation of the radiopharmaceutical composition.

Use for Imaging

Another aspect of the present invention is the use of a radiopharmaceutical composition as defined above, for the manufacture of an imaging agent for imaging a tumor in a mammal.

The peptide as defined above has a selective affinity for SSTR2 receptor, thus a radiopharmaceutical composition as defined above is particularly useful for imaging SSTR2 receptor positive tumors, such as neuroendocrine tumors (NETs), and particularly gastroenteropancreatic neuroendocrine tumors (GEP NETs), or tumors of prostate, breast, lung or lymphoma cancer. In a preferred embodiment, a radiopharmaceutical composition as defined above is useful for the manufacture of an imaging agent for GEP NETs in a mammal. Such imaging agent is useful not only for the confirmation of diagnosis but also for patient management, such as detection and localization of suspected tumors.

Method of Imaging

Another aspect of the present invention is a method of imaging SSTR2 receptor positive tumors within human body, said method comprising:
administering to said human a detectable quantity of a radiopharmaceutical composition as defined above,
allowing sufficient time for the active ingredient of the radiopharmaceutical composition to become associated with one or more said SSTR2 receptors, and
detecting said active ingredient associated with one or more said SSTR2 receptors, by submitting said human to external imaging, typically by radioactive scanning or by magnetic resonance imaging, in order to allow detection and localization of said tumors in the body.

The radiopharmaceutical composition as defined above may be administered parenterally, preferably intravenously, in the form of injectable solution or suspension, preferably in a single injection. The radiopharmaceutical composition may also be administered by infusion.

The appropriate radioactivity of one injection may be in the range of 10.0 to 255.0 MBq, preferably in the range of 40 to 200 MBq. Examples of appropriate radioactivity are 40-80 MBq, 100-140 MBq and 160-200 MBq.

The appropriate peptide dose of one injection may be in the range of 1 to 100 µg, preferably in the range of 5 to 60 µg. Examples of appropriate peptide dose are 5-20 µg and 30-45 µg.

The radiopharmaceutical composition may preferably be prepared shortly before the administration to human, i.e. the radiolabeling of the NODAGA-peptide with a radionuclide cation such as $^{68}Ga^{3+}$, may be performed shortly before administration.

EXPERIMENTAL PART

Figure 1:
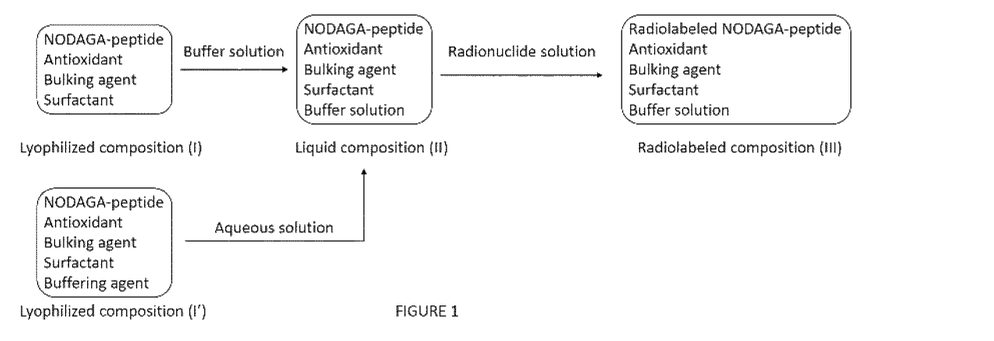
FIG. 1 schematically represents the process for preparing a radiolabeled composition (III) according to the invention. Two options are presented to obtain the liquid composition (II): either from a lyophilized composition (I) or from a lyophilized composition (I') as defined above. In the first option, a lyophilized composition (I) according to the invention is reconstituted with a buffer solution to provide the liquid composition (II). In the second option, a lyophilized composition (I') according to the invention is reconstituted with water to provide the liquid composition (II). A radionuclide solution is then added to the thereby obtained liquid composition (II) to provide the radiolabeled composition (III).
Figure 2:
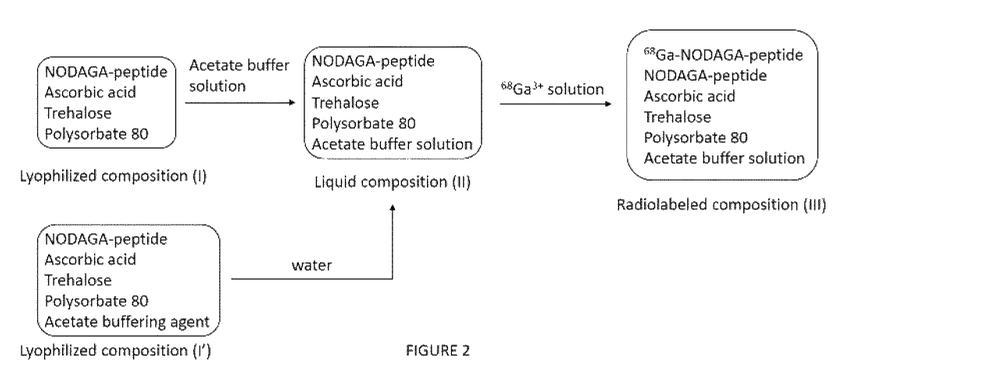
FIG. 2 schematically represents the process for preparing a preferred embodiment of the radiolabeled composition (III) according to the invention. Two options are presented to obtain the liquid composition (II): either from a lyophilized composition (I) or from a lyophilized composition (I') as defined above. In the first option, a lyophilized composition (I) according to the invention is reconstituted with an acetate buffer to provide the liquid composition (II). In the second option, a lyophilized composition (I') according to the invention is reconstituted with water to provide the liquid composition (II). A $^{68}Ga^{3+}$ solution is then added to the thereby obtained liquid composition (II) to provide the radiolabeled composition (III).

Example 1: Preparation of a Lyophilized Composition (I)

500 g of trehalose and 50 g of ascorbic acid were added in a vessel containing 7 L of water for injection (WFI). After dissolution, 1 g of polysorbate 80 then NODAGA-peptide (INN: satoreotide trizoxetan) acetate salt (mass equivalent to 500 mg of pure NODAGA-peptide) were successively added. The mixture was stirred until complete homogenization and solubilisation of the NODAGA-peptide. Further approximately 3 L of WFI were then added. The solution thus obtained was dispensed in vials (1 mL of solution, i.e. 50 μg of pure NODAGA-peptide per vial) and lyophilized according to an adequate freeze-drying cycle to get the lyophilized composition (I).

Example 2: Preparation of a Liquid Composition (II)

A lyophilized composition (I) prepared in a vial in example 1 was reconstituted with 1M sodium acetate buffer solution (pH 5) to obtain liquid composition (II) with a concentration of NODAGA-peptide of about 50 μg/mL.

Example 3: Preparation of a Radiolabeled Composition (III)

To the liquid composition (II) prepared according to example 2 were added 5 mL of an eluate from $^{68}Ge/^{68}Ga$ generator for radiolabeling to obtain radiolabeled composition (III).

Example 4: Stability Study of Lyophilized Compositions

Pharmaceutical lyophilized compositions 1 to 10 have been prepared according to the process described in example 1. The amount of the API per vial (i.e. NODAGA-peptide in base form) given in Table 1 below is expressed in μg. The percentage of surfactant is given by weight relative to the total weight of dry material.

The stability of these lyophilized compositions (I) has been studied under the different conditions: 40° C./75% RH (RH: relative humidity), 25° C./60% RH, and 5° C. A stability study measures the evolution over time of the amount of API and the evolution over time of the amount of impurities. When the initial amount of API is maintained over time and the amount of impurities does not significantly increase, a pharmaceutical composition is said stable.

TABLE 1

| Lyophilized compositions | API (μg) | antioxidant | bulking agent | surfactant |
|---|---|---|---|---|
| 1 | 50 | ascorbic acid 5 mg | trehalose 30 mg | — |
| 2 | 50 | methionine 5 mg | trehalose 30 mg | — |
| 3 | 100 | ascorbic acid 5 mg | trehalose 30 mg | — |
| 4 | 50 | ascorbic acid 5 mg | trehalose 50 mg | — |
| 5 | 50 | methionine 5 mg | trehalose 50 mg | — |
| 6 | 50 | ascorbic acid 5 mg | trehalose 50 mg | poloxamer 188 0.1 mg |
| 7 | 50 | ascorbic acid 5 mg | trehalose 50 mg | polysorbate 80 0.1 mg |
| 8 | 50 | methionine 5 mg | trehalose 50 mg | poloxamer 188 0.1 mg |
| 9 | 50 | ascorbic acid 5 mg | trehalose 100 mg | polysorbate 80 0.1 mg |
| 10 | 50 | ascorbic acid 8 mg | trehalose 100 mg | polysorbate 80 0.1 mg |

The stability data at these different conditions and after 2 weeks (2W), 1 month (1M), 2 months (2M), 3 months (3M), 6 months (6M), 9 months (9M), 12 months (12M), 18 months (18M) or 24 months (24M) are summarized in Tables 2-4 below. The percentage of impurities is the sum of the percentages of all impurities detected by UPLC (Ultra Performance Liquid Chromatography) and with a percentage over 0.1% (limit of detection). The water content was determined using a coulometer.

TABLE 2 conditions 40° C./75% RH

| | composition 1 | | | | | composition 2 | | | | | composition 3 |
|---|---|---|---|---|---|---|---|---|---|---|---|
| | T0 | 2 W | 1 M | 2 M | 3 M | T0 | 2 W | 1 M | 2 M | 3 M | T0 |
| Water content (%) | 1.5 | 3.4 | 3.9 | 3.9 | 4.4 | 0.1 | 1.9 | 3.3 | 2.6 | 3.0 | 1.5 |
| API content (μg/vial) | 49.0 | 49.6 | 48.7 | 48.9 | 48.8 | 47.0 | 48.2 | 47.1 | 46.3 | 45.9 | 99.9 |
| Impurities (%) | 2.2 | 1.9 | 2.1 | 1.9 | 2.0 | 2.8 | 2.9 | 3.7 | 4.2 | 4.5 | 2.2 |

TABLE 2-continued conditions 40° C./75% RH

| | composition 3 | | | | composition 4 | | | | | |
|---|---|---|---|---|---|---|---|---|---|---|
| | 2 W | 1 M | 2 M | 3 M | T0 | 2 W | 1 M | 2 M | 3 M | 6 M |
| Water content (%) | 3.4 | 3.8 | 4.0 | 4.1 | 1.0 | 2.4 | 2.7 | 3.0 | 3.0 | 2.5 |
| API content (μg/vial) | 100.1 | 100.5 | 94.5 | 98.5 | 48.2 | 48.9 | 50.0 | 48.5 | 48.5 | 46.8 |
| Impurities (%) | 1.5 | 1.6 | 1.6 | 1.9 | 2.5 | 1.7 | 1.5 | 1.8 | 1.8 | 2.9 |

| | composition 5 | | | | | composition 7 | | | | | composition 9 | | | | composition 10 | | | |
|---|---|---|---|---|---|---|---|---|---|---|---|---|---|---|---|---|---|---|
| | T0 | 2 W | 1 M | 2 M | 3 M | T0 | 2 W | 1 M | 3 M | 6 M | T0 | 2 W | 1 M | 2 M | T0 | 2 W | 1 M | 2 M |
| Water content (%) | 0.1 | 1.7 | 2.0 | 2.2 | 2.3 | 1.1 | 2.5 | 2.9 | — | 2.6 | 0.5 | 1.2 | — | — | 0.8 | 1.4 | — | — |
| API content (μg/vial) | 46.1 | 48.3 | 49.4 | 48.6 | 48.9 | 57.3* | 47.9 | 48.0 | 46.6 | 46.8 | 46.6 | 46.3 | 47.1 | 45.4 | 46.0 | 46.0 | 46.1 | 45.4 |
| Impurities (%) | 2.7 | 1.8 | 1.8 | 1.8 | 2.3 | 2.3 | 2.5 | 2.5 | 2.7 | 3.9 | 2.0 | 2.3 | 3.0 | 2.6 | 2.2 | 2.2 | 3.8 | 2.9 |

*calibration curve without surfactant

TABLE 3 conditions 25° C./60% RH

| | composition 1 | | | composition 2 | | | composition 3 | | | composition 4 | | | | composition 5 | | |
|---|---|---|---|---|---|---|---|---|---|---|---|---|---|---|---|---|
| | T0 | 1 M | 2 M | T0 | 1 M | 2 M | T0 | 1 M | 2 M | T0 | 1 M | 2 M | 6 M | T0 | 1 M | 2 M |
| Water content (%) | 1.5 | 2.9 | 3.4 | 0.1 | 1.6 | 2.0 | 1.5 | 3.1 | 3.5 | 1.0 | 2.1 | 2.4 | 2.2 | 0.1 | 1.3 | 1.6 |
| API content (μg/vial) | 49.0 | 48.3 | 48.4 | 47.0 | 47.2 | 46.6 | 99.9 | 98.9 | 94.4 | 48.2 | 48.3 | 48.6 | 47.7 | 46.1 | 47.8 | 47.3 |
| Impurities (%) | 2.2 | 2.1 | 1.8 | 2.8 | 2.6 | 2.7 | 2.2 | 1.4 | 1.2 | 2.5 | 1.7 | 1.4 | 2.3 | 2.7 | 1.8 | 1.8 |

| | composition 6 | | | composition 7 | | | | | | composition 8 | | | composition 9 | | | composition 10 | | |
|---|---|---|---|---|---|---|---|---|---|---|---|---|---|---|---|---|---|---|
| | T0 | 1 M | 2 M | T0 | 1 M | 2 M | 6 M | 9 M | 12 M | T0 | 1 M | 2 M | T0 | 1 M | 2 M | T0 | 1 M | 2 M |
| Water content (%) | 1.1 | 2.1 | — | 1.1 | 2.1 | 2.4 | 2.1 | — | 2.4 | 0.1 | 1.2 | — | 0.5 | — | — | 0.8 | — | — |
| API content (μg/vial) | 56.2* | 48.6 | — | 57.3* | 48.9 | 47.3 | 47.4 | 49.0 | 48.6 | 56.4* | 48.3 | — | 46.6 | 46.4 | — | 46.0 | 45.8 | — |
| Impurities (%) | 2.1 | 1.7 | — | 2.3 | 1.6 | 2.7 | 2.4 | 1.8 | 2.0 | 2.6 | 1.9 | — | 2.0 | 4.9 | — | 2.2 | 6.2 | — |

*calibration curve without surfactant

TABLE 4 conditions 5° C.

| | composition 1 | | | composition 2 | | | composition 3 | | | composition 4 | | | | composition 5 | | |
|---|---|---|---|---|---|---|---|---|---|---|---|---|---|---|---|---|
| | T0 | 1 M | 2 M | T0 | 1 M | 2 M | T0 | 1 M | 2 M | T0 | 1 M | 2 M | 6 M | T0 | 1 M | 2 M |
| Water content (%) | 1.5 | 1.9 | 2.1 | 0.1 | 0.5 | 0.7 | 1.5 | 2.0 | 2.1 | 1.0 | 1.2 | 1.4 | 1.1 | 0.1 | 0.4 | 0.5 |
| API content (μg/vial) | 49.0 | 48.0 | 47.7 | 47.0 | 46.9 | 45.4 | 99.9 | 98.5 | 93.3 | 48.2 | 47.7 | 47.6 | 47.4 | 46.1 | 45.7 | 46.5 |
| Impurities (%) | 2.2 | 1.8 | 1.9 | 2.8 | 2.1 | 2.4 | 2.2 | 1.4 | 1.2 | 2.5 | 1.5 | 1.7 | 2.4 | 2.7 | 1.8 | 1.6 |

| | composition 6 | | | composition 7 | | | | | | | | composition 8 | | composition 9 | | composition 10 | |
|---|---|---|---|---|---|---|---|---|---|---|---|---|---|---|---|---|---|
| | T0 | 1 M | 2 M | T 0 | 1 M | 2 M | 6 M | 9 M | 12 M | 18 M | 24 M | T0 | 1 M | T0 | 1 M | T0 | 1 M |
| Water content (%) | 1.1 | 1.2 | — | 1.1 | 1.3 | 1.4 | 1.0 | 1.2 | 1.5 | 1.8 | 1.9 | 0.1 | 0.3 | 0.5 | — | 0.8 | — |
| API content (μg/vial) | 56.2* | 47.7 | — | 57.3* | 48.6 | 48.0 | 47.4 | 49.2 | 49.1 | 51.0 | 52.8 | 56.4* | 49.0 | 46.6 | 46.4 | 46.0 | 46.1 |
| Impurities (%) | 2.1 | 1.8 | — | 2.3 | 1.9 | 2.3 | 2.5 | 1.6 | 2.0 | 1.8 | 1.9 | 2.6 | 1.8 | 2.0 | 3.8 | 2.2 | 4.1 |

*calibration curve without surfactant

The invention claimed is:

1. A receptor-selective somatostatin peptide antagonist composition comprising:
a NODAGA-peptide of formula (I), —Phe-(D-Cys)-Phe-(D-Phe)-Lys-Thr-Cys-(D-tyr)-NH$_2$ or a salt thereof;
an antioxidant selected from ascorbic acid or a salt thereof and methionine; and
a bulking agent, wherein the bulking agent is trehalose.

2. The composition of claim 1, further comprising a surfactant.

3. The composition of claim 1, wherein the weight ratio of the antioxidant over the NODAGA-peptide is at least 50.

4. The composition of claim 2, wherein the surfactant is a polysorbate.

5. The composition of claim 1, wherein the composition is in a lyophilized form.

6. The composition of claim 5, wherein;
the NODAGA-peptide is in a salt form and is present in the range of 0.02% to 0.20% by weight relative to the total weight of the composition;
the antioxidant is present in the range of 4% to 15% by weight relative to the total weight of the composition;
the bulking agent is present in the range of 80% to 96% by weight relative to the total weight of the composition; and/or
the composition further comprises a surfactant, wherein the surfactant is present in the range of 0.01% to 0.36% by weight relative to the total weight of the composition.

7. The composition of claim 6, wherein the antioxidant is ascorbic acid.

8. The composition of claim 6, wherein the surfactant is a polysorbate.

9. The composition of claim 5, comprising:
NODAGA-peptide acetate salt in the range of 0.02% to 0.20% by weight;
ascorbic acid in the range of 4% to 15% by weight;
trehalose in the range of 80% to 96% by weight; and
a surfactant, wherein the surfactant is a polysorbate in the range of 0.10% to 0.36% by weight;
wherein the NODAGA-peptide acetate salt, ascorbic acid, trehalose and polysorbate, taken together, represent 98% of the total weight of the lyophilized composition.

10. The composition of claim 5, further comprising a buffering agent.

11. The composition of claim 1, wherein the composition is in a liquid aqueous form.

12. The composition of claim 11, comprising:
ascorbic acid;
a polysorbate; and
a buffer solution; and
wherein the NODAGA-peptide is in a salt form.

13. The composition of claim 11, wherein the NODAGA-peptide is in a salt form and is present at a concentration of 0.02 to 0.12 mg/mL.

14. The composition of claim 1, wherein the composition is a radiolabeled composition.

15. The composition of claim 14, wherein the composition comprises:
ascorbic acid;
a polysorbate; and
a buffer solution; and
the NODAGA-peptide is $^{68}$Ga$^{3+}$ radiolabeled.

16. A kit comprising a first vial containing the composition of claim 1, wherein the composition is in a lyophilized form.

17. The kit of claim 16, further comprising a second vial containing a sterile reconstitution solution comprising a buffer solution.

18. A method for imaging a tumor in a mammal, comprising administering the radiolabeled composition of claim 14 to the mammal, optionally wherein the mammal is a human.

19. The method of claim 18, wherein the tumor is a SSTR2 receptor positive tumor and the method further comprises detecting the radiolabeled composition by exposing the mammal to external imaging, by radioactive scanning or by magnetic resonance imaging.

* * * * *